C. H. & H. E. Davidson,
Syringe,
No. 1,940. Reissued Apr. 25. 1865.
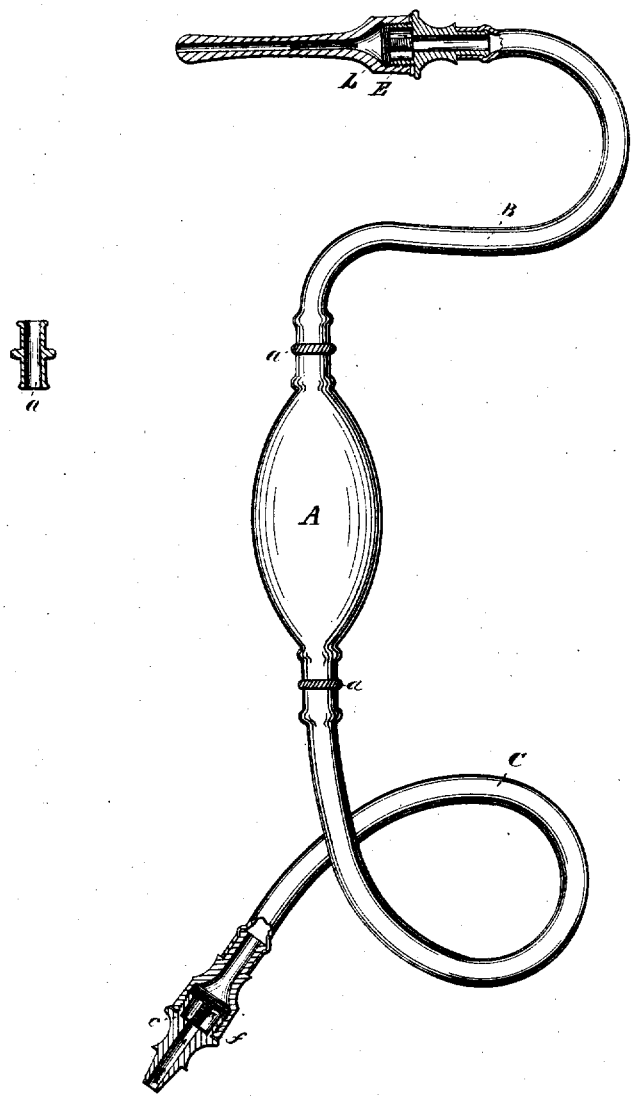
Witnesses
N. G. Lombard
J. B. Crosby
A. Refson
C. Hayes
Inventors.
Chas. H. Davidson
Hannah E. Davidson
AM. PHOTO-LITHO. CO. N.Y. (OSBORNE'S PROCESS.)

UNITED STATES PATENT OFFICE.

HAMILTON D. LOCKWOOD, OF CHARLESTOWN, MASSACHUSETTS, ASSIGNEE OF C. H. AND H. E. DAVIDSON.

IMPROVEMENT IN ENEMA-SYRINGES.

Specification forming part of Letters Patent No. 16,956, dated March 31, 1857; Reissue No. 1,940, dated April 25, 1865.

*To all whom it may concern:*

Be it known that CHARLES H. DAVIDSON, of Charlestown, in the county of Middlesex, in the State of Massachusetts, and HERMAN E. DAVIDSON, of Gloucester, in the county of Essex, in the said State, invented jointly a new and Improved Syringe, of which the following, taken in connection with the accompanying drawings, is a description sufficiently clear and exact to enable those skilled in the art to practice said invention.

This invention consists in a syringe which is composed of an elastic bulb provided with two flexible tubes and a suitable valvular arrangement, all being so organized that by compressing the bulb its contents shall be expelled through one tube, while by the expansion of the bulb, consequent upon its own elasticity, it will be filled with whatever fluid the salient end of the other tube is immersed in.

This invention is particularly useful and capable of universal application in that any person may cleanse or inject any natural outlet from the body without aid from a second person, and any desired quantity of injection or enema may be administered without removal of the salient end of the injecting tube from the body, while from the flexible character of the tubes no injurious or hurtful strain is brought upon the body, which, with the vessel containing the fluid, may be in any position desired within reasonable limits.

Referring to the drawings, A denotes a hollow chamber, bulb, or sack, made of rubber or other suitable material, of sufficient elasticity to recover its form when compressed. The flexible tubes are denoted by B and C, the former being the outlet-passage from the bulb A, and the latter the inlet-passage to the bulb. These tubes are best made of rubber. The tubes B and C are provided with suitable valve-boxes E and F. In E is located the delivery or outlet valve *b*, opening outward, and in F is placed the inlet or suction valve *c*, opening inward. The salient end of the tube B is to be provided with terminations of such shape and material as to be adapted to the requirements of any passage to be injected, and the salient end of the tube C should be provided with a termination suited to sink in fluid and to admit its passage freely into the tube. Suitable coupling-pieces (denoted by *a*) serve to connect the tubes B and C to the bulb.

The operation of this instrument is as follows: Immerse the end of the inlet-tube C in the enema, compress the bulb with the hand, which will expel the air from within it through the tube B; then, releasing the grasp of the hand, the bulb will recover its form by virtue of its elascity, and the vacuum thus formed, more or less perfect, will be filled by the enema. Now insert the salient end of tube B in the orifice to be injected, and repeat the operation of compressing the bulb until the required quantity of injection is administered.

The spheroidal shape of the bulb, as shown, is deemed preferable to any other, as it is best adapted for the grasp of the hand and easily resumes its shape after compression.

The arrangement of the bulb with its axis, as a continuation of the axes of the tubes is, preferable to any other, on account of obtaining a direct flow of fluid through the instrument and because the whole instrument readily drains itself if allowed to hang pendent from the end of tube C.

What is claimed as the invention of CHARLES H. DAVIDSON and HERMAN E. DAVIDSON is—

A syringe having an elastic bulb or chamber, flexible tubes, and a suitable valvular arrangement, when organized so as to operate substantially as described.

In witness whereof I have hereunto set my hand this 9th day of February, A. D. 1865.

H. D. LOCKWOOD.

In presence of—
J. B. CROSBY,
W. B. GLEASON.